(12) United States Patent
Graf et al.

(10) Patent No.: US 8,877,926 B2
(45) Date of Patent: Nov. 4, 2014

(54) PROCESS FOR THE PREPARATION OF ENANTIOMERIC FORMS OF 2,3-DIAMINOPROPIONIC ACID DERIVATIVES

(71) Applicant: Sanofi, Paris (FR)

(72) Inventors: Claus-Dieter Graf, Frankfurt am Main (DE); Joerg Rieke-Zapp, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/763,975

(22) Filed: Feb. 11, 2013

(65) Prior Publication Data

US 2013/0211085 A1 Aug. 15, 2013

Related U.S. Application Data

(63) Continuation of application No. PCT/EP2011/063504, filed on Aug. 5, 2011.

(60) Provisional application No. 61/428,336, filed on Dec. 30, 2010.

(30) Foreign Application Priority Data

Aug. 12, 2010 (EP) .................................. 10305884

(51) Int. Cl.
*C07D 239/42* (2006.01)
*C07D 213/74* (2006.01)

(52) U.S. Cl.
CPC ............ *C07D 239/42* (2013.01); *C07D 213/74* (2013.01)
USPC ........................................................ 544/332

(58) Field of Classification Search
USPC .................................. 544/330, 332
See application file for complete search history.

(56) References Cited

U.S. PATENT DOCUMENTS

| 7,285,560 | B2 | 10/2007 | Ritzeler et al. |
| 7,342,029 | B2 | 3/2008 | Ritzeler et al. |
| 7,462,638 | B2 | 12/2008 | Michaelis et al. |
| 8,232,395 | B2 | 7/2012 | Graeser et al. |
| 2007/0142417 | A1 | 6/2007 | Haddad et al. |
| 2007/0244139 | A1 | 10/2007 | Ritzeler et al. |
| 2009/0069358 | A1 | 3/2009 | Michaelis et al. |
| 2012/0271051 | A1 | 10/2012 | Graeser et al. |

FOREIGN PATENT DOCUMENTS

| WO | WO 01/30774 | 5/2001 |
| WO | WO 2004/022553 | 3/2004 |

OTHER PUBLICATIONS

International Search Report for WO2012/019967 dated February 16, 2012.
Flynn, et al., A Mild Two-Step Method for the Hydrolysis/Methanolysis of Secondary Amides and Lactams, J. Org. Chem., (1983), vol. 48, pp. 2424-2426.
Burk, et al., A Mild Amide to Carbamate Transformation, J. Org. Chem., (1997), vol. 62, pp. 7054-7057.
Abdioui, et al., Synthese D'Aminoacides Cydopropaniques par Reaction du Diazoacetate D'Ethyle sur des Methyleneglycinates N-Proteges, K. El Abdioui et al., Bull. Soc. Chim. Belg. (1997), vol. 106, pp. 425.
Ferreira, et al., High Yielding Synthesis of Dehydroamino Acid and Dehydropeptide Derivatives, J. Chem. Soc., Perkin Trans. 1, (1999), pp. 3697-3703.
Matsukawa et al., Syntheses of 2-Aminopyrimidine Derivatives, Yakugaku Zasshi, (1951), vol. 71, pp. 933-935.

*Primary Examiner* — Golam M Shameem
*Assistant Examiner* — Laura Daniel
(74) *Attorney, Agent, or Firm* — Kelly L. Bender

(57) ABSTRACT

The disclosure relates to a process for the preparation of the enantiomeric forms of 2,3-diaminopropionic acid derivatives of formula I,

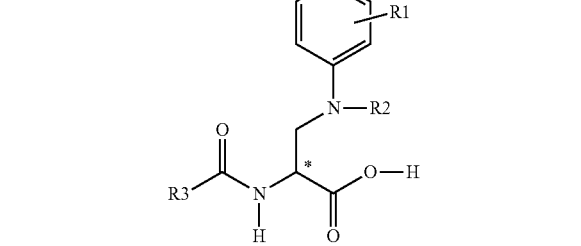

wherein R1, R2 and R3 are defined as in the disclosure, by racemate resolution. The separation of the racemate into its enantiomers takes place through formation of diastereomeric salts upon addition of an enantiomerically pure auxiliary, and subsequent separation by fractional crystallization.

3 Claims, No Drawings

PROCESS FOR THE PREPARATION OF ENANTIOMERIC FORMS OF 2,3-DIAMINOPROPIONIC ACID DERIVATIVES

This application is a continuation of International Application No. PCT/EP2011/063504, filed Aug. 5, 2011, which is incorporated herein by reference in its entirety; which claims the benefit of priority of U.S. Provisional Application No. 61/428,336, filed Dec. 30, 2010, and European Patent Application No. 10305884.8, filed Aug. 12, 2010.

The invention relates to a process for the preparation of the enantiomeric forms of 2,3-diaminopropionic acid derivatives of formula I by racemate resolution.

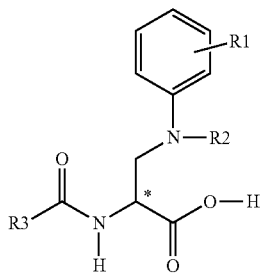

The separation of the racemate into its enantiomers takes place through formation of diastereomeric salts upon addition of an enantiomerically pure auxiliary, and subsequent separation by fractional crystallization. The compounds of formula I are suitable intermediates for the preparation of IkB kinase inhibitors as described in WO 01/30774 A1, WO 2004/022553 A1 and US 2007/0142417 A1, for example.

It is known that enantiomerically pure 2,3-diaminopropionic acid derivatives are used as building blocks for the synthesis of active pharmaceutical ingredients, including IkB kinase inhibitors (cf. WO 2004/022553 A1 and US 2007/0142417 A1). Since these building blocks have hitherto only been able to be produced in isolated cases via an asymmetric synthesis, the enantiomerically pure compounds are usually obtained via a laborious chromatographic separation of the racemate on a chiral stationary phase. These chromatographic methods are very costly in terms of apparatus time, are limited to small amounts, and use enormous amounts of solvents. Moreover, the chiral stationary phases are very expensive. This access route to the desired enantiomers therefore is not very practicable with regard to an industrial production.

It is an object of the present invention to find a technical process for the preparation of the compounds of formula I which does not have the stated disadvantages.

It has now been found that the separation of the racemate into the enantiomers of formula I through formation of diastereomeric salts upon addition of an enantiomerically pure auxiliary can also be achieved in the case of compounds of formula II defined below. The preparation of the compound of formula I is thereby effected in a time-saving and cost-saving way with high yields and high enantiomeric purity in a manner which is technically simple to carry out. It also allows problem-free scale-up.

The invention therefore relates to a process for obtaining a compound of formula I,

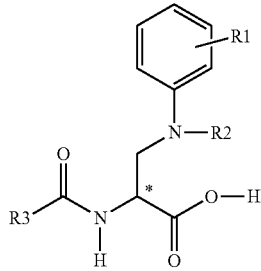

wherein

R1 is a hydrogen atom, F, Cl, I, Br, $(C_1\text{-}C_4)$-alkyl or —CN;

R2 is a heteroaryl residue selected from the series consisting of pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of $(C_1\text{-}C_5)$-alkyl, $(C_1\text{-}C_5)$-alkoxy, halogen, nitro, amino, trifluoromethyl, hydroxy, hydroxy-$(C_1\text{-}C_4)$-alkyl-, methylenedioxy, ethylenedioxy, formyl, acetyl, cyano, hydroxycarbonyl-, aminocarbonyl- and $(C_1\text{-}C_4)$-alkoxycarbonyl-, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted once, twice or three times, independently of each other, by substituents selected from the series consisting of $(C_1\text{-}C_5)$-alkyl, $(C_1\text{-}C_5)$-alkoxy, halogen, nitro, amino, trifluoromethyl, hydroxy, hydroxy-$(C_1\text{-}C_4)$-alkyl-, methylenedioxy, ethylenedioxy, formyl, acetyl, cyano, hydroxycarbonyl-, aminocarbonyl- and $(C_1\text{-}C_4)$-alkoxycarbonyl-;

R3 is a hydrogen atom, or $(C_1\text{-}C_4)$-alkyl, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —$NO_2$, —O—$(C_1\text{-}C_4)$-alkyl, F, Cl and Br, or —O—$C(CH_3)_3$, or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —$NO_2$, —O—$CH_3$, F, Cl and Br, and wherein R7 is a hydrogen atom or $(C_1\text{-}C_4)$-alkyl;

which comprises
a) mixing a compound of formula II,

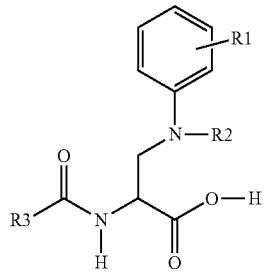

wherein R1, R2 and R3 are defined as in the compound of formula I, in an organic solvent or a mixture of organic solvents with an enantiomerically pure auxiliary;
b) separating the salt composed of enantiomerically pure auxiliary and compound of formula I, by fractional crystallization; and
c) isolating the compound of formula I from the salt composed of enantiomerically pure auxiliary and compound of formula I.

In one embodiment, the invention relates to a process for obtaining a compound of formula I, wherein
R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R3 is phenyl, methyl or —O—C(CH$_3$)$_3$;
which comprises
a) mixing a compound of formula II, wherein R1, R2 and R3 are defined as in the compound of formula I, in an organic solvent or a mixture of organic solvents selected from the series consisting of n-butyl acetate, ethyl acetate, isopropyl acetate, diisopropyl ether, methyl tert-butyl ether and diethyl ether, with an enantiomerically pure auxiliary selected from the series consisting of (S)-1-phenylethylamine, (R)-1-phenylethylamine, (S)-1-naphthylethylamine, (R)-1-naphthylethylamine, (S)-1-cyclohexylethylamine, (R)-1-cyclohexylethylamine, (S)-1-cyclopropylethylamine and (R)-1-cyclopropylethylamine;
b) separating the salt composed of enantiomerically pure auxiliary and compound of formula I, by fractional crystallization; and
c) isolating the compound of formula I from the salt composed of enantiomerically pure auxiliary and compound of formula I.

In one embodiment, the group R1 in the compounds and processes according to the invention outlined above and below, such as in the compounds of formulae I and II, is a hydrogen atom, F or Cl, in another embodiment it is a hydrogen atom or F, in another embodiment it is a hydrogen atom.

In one embodiment, the group R2 in the compounds and processes according to the invention outlined above and below, such as in the compounds of formulae I and II, is a heteroaryl residue selected from the series consisting of pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-, and in another embodiment is selected from the series consisting of pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy and halogen, and in another embodiment is unsubstituted or is substituted once, twice or three times, independently of each other, by substituents selected from the series consisting of (C$_1$-C$_5$)-alkyl and halogen. In another embodiment R2 is phenyl, pyridinyl or pyrimidinyl, in another embodiment it is phenyl or pyridinyl, in another embodiment it is pyridinyl, pyrimidinyl or thiazolyl, in another embodiment it is pyridinyl or pyrimidinyl, in another embodiment it is phenyl, in another embodiment it is pyridinyl, in another embodiment it is pyrimidinyl, in another embodiment it is thiazolyl, wherein phenyl, pyridinyl, pyrimidinyl and thiazolyl are unsubstituted or substituted by fluorine or chlorine, and in another embodiment are unsubstituted or substituted by fluorine, and in another embodiment are unsubstituted. Pyridinyl representing R2 can be any one or more of the groups pyridin-2-yl, pyridin-3-yl and pyridin-4-yl, pyrimidinyl representing R2 can be any one or more of the groups pyrimidin-2-yl, pyrimidin-4-yl and pyrimidin-5-yl, and thiazolyl representing R2 can be any one or of more the groups thiazol-2-yl, thiazol-4-yl and thiazol-5-yl.

In one embodiment, the group R3 in the compounds and processes according to the invention outlined above and below, such as in the compounds of formulae I and II, is methyl, —O—C(CH$_3$)$_3$ or —O—CH(R7)-aryl, wherein R7 is a hydrogen atom and aryl is unsubstituted phenyl, in another embodiment it is —O—C(CH$_3$)$_3$ or —O—CH(R7)-aryl, wherein R7 is a hydrogen atom and aryl is unsubstituted phenyl, in another embodiment it is methyl, in another embodiment it is —O—C(CH$_3$)$_3$, i.e. a tert-butoxy group, in another embodiment it is —O—CH(R7)-aryl, wherein R7 is a hydrogen atom and aryl is unsubstituted phenyl, i.e. a benzyloxy group.

The present invention relates to all combinations of definitions of compounds and processes with one or more embodiments and/or other features and/or specific denotations of groups or features specified herein.

The terms "(C$_1$-C$_3$)-alkyl", "(C$_1$-C$_4$)-alkyl" and "(C$_1$-C$_5$)-alkyl" are understood as meaning hydrocarbon residues the carbon chain of which is straight-chain or branched and comprise 1, 2 or 3 carbon atoms, or 1, 2, 3 or 4 carbon atoms, or 1, 2, 3, 4 or 5 carbon atoms, respectively. Examples of alkyl groups are methyl, ethyl, propyl, isopropyl, butyl, isobutyl, tert-butyl and pentyl.

The term "—CH(R7)-" is understood as meaning straight-chain or branched hydrocarbon residues such as methylene, ethylene, isopropylene, isobutylene or pentylene. An example of the residue "—CH(R7)-aryl", in which R7 is a hydrogen atom and aryl is phenyl, is the residue benzyl.

If R1 is a hydrogen atom (H), this means that the phenyl residue in the compounds of formulae I and II and other compounds defined below, which carries the group R1, is an unsubstituted phenyl residue. If R1 has another meaning than a hydrogen atom, such as F, Cl, I or Br, this means that in the phenyl residue carrying R1 a hydrogen atom has been replaced by the respective group or atom, i.e., the said phenyl residue is a substituted phenyl residue carrying the respective group or atom as substituent. Such substituents can be present in any position of the phenyl residue, including the 2-position, the 3-position and the 4-position. It applies in general to all groups in the compounds of formulae I and II and other compounds defined below, for example to heteroaryl residues and aryl residues representing R2, that substituents can be present in any suitable position, and that substituents can be identical or different if more than one substituent is present in a group.

The term "halogen" is understood as meaning fluorine (F), chlorine (Cl), iodine (I) and bromine (Br). In one embodiment, halogen is F or Cl, in another embodiment it is F.

The asterisk next to a carbon atom in formula I and the formulae of other compounds defined below means that the respective compound is present as an individual enantiomer, either as R-enantiomer or as S-enantiomer, where the term "present as an individual enantiomer" is understood as meaning that the compound is present as a substantially pure enantiomer with regard to the presence of the opposite enantiomer. In one embodiment, the ee value, i.e. the enantiomeric excess in percent, of such a substantially pure enantiomer according to the invention is >90%, in another embodiment >95%, in another embodiment >98%, in another embodiment >99%, where the ee value of a specific sample obtained according to the invention, which is desired for the further use of the sample and which is obtainable under the employed conditions, naturally varies depending on the peculiarities of the specific case.

The term "enantiomerically pure auxiliary" is understood as meaning enantiomerically pure amine compounds with at least one center of chirality which are able to form a diastereomeric salt with the carboxylic acids of formulae I and II. In one embodiment, such an auxiliary with one center of chirality is employed. In another embodiment, such an auxiliary is a compound from the substance classes of chiral 1-aryl-ethylamines, 1-cycloalkyl-ethylamines, 1-aryl-propylamines and 1-cycloalkyl-propylamines, wherein aryl is, for example, phenyl or naphthyl including 1-naphthyl and 2-naphthyl, and is unsubstituted or substituted once, twice or three times, independently of each other, by substituents selected from the series consisting of ($C_1$-$C_5$)-alkyl, ($C_1$-$C_5$)-alkoxy and halogen, and cycloalkyl is, for example, cyclopropyl or cyclohexyl. In one embodiment, the enantiomerically pure auxiliary is selected from the series consisting of (S)-1-phenylethylamine, (R)-1-phenylethylamine, (S)-1-phenylpropylamine, (R)-1-phenylpropylamine, (S)-1-naphthylethylamine, (R)-1-naphthylethylamine, (S)-1-cyclohexylethylamine, (R)-1-cyclohexylethylamine, (S)-1-cyclopropylethylamine and (R)-1-cyclopropylethylamine, in another embodiment from the series consisting of (S)-1-phenylethylamine and (R)-1-phenylethylamine, and in another embodiment it is (S)-1-phenylethylamine. The chemical purity of the employed enantiomerically pure auxiliary should be >95% and the enantiomeric excess >90%. The chirality of the auxiliary to be employed in a specific case depends on the peculiarities of the case and the desired chirality of the compound of formula I.

The term "fractional crystallization" is understood as meaning a separation method which utilizes differences in the solubility of the substances in order to separate crystals. The crystallization can be caused by concentration changes, changes in the temperature or other triggers such as the Use of seed crystals, for example.

For the fractional crystallization method, the racemic compound of formula II can be suspended or dissolved in a suitable solvent or solvent mixture. Suitable solvents are, for example, esters such as n-butyl acetate, ethyl acetate or isopropyl acetate, and ethers such as diisopropyl ether, methyl tert-butyl ether or diethyl ether. In one embodiment, solvents selected from the series consisting of n-butyl acetate, ethyl acetate, isopropyl acetate, diisopropyl ether and methyl tert-butyl ether, in another embodiment from the series consisting of n-butyl acetate and diisopropyl ether, or mixtures thereof, are employed. An enantiomerically pure auxiliary is then added to this solution or sUspension with stirring, for example (S)-1-phenylethylamine, (R)-1-phenylethylamine, (S)-1-naphthylethylamine, (R)-1-naphthylethylamine, (S)-1-cyclohexylethylamine, (R)-1-cyclohexylethylamine, (S)-1-cyclopropylethylamine, (R)-1-cyclopropylethylamine, in particular (S)-1-phenylethylamine or (R)-1-phenylethylamine. The order in which the compound of formula II and the enantiomerically pure auxiliary are introduced, can also be inverted. The molar ratio of the compound of formula II to the enantiomerically pure auxiliary is advantageoUsly from about 0.5 to about 1.1. In one embodiment, the molar ratio of the compound of formula II to the enantiomerically pure auxiliary is from about 0.9 to about 1.1, in another embodiment from about 0.9 to about 1.0, in another embodiment from about 1.0 to about 1.1.

The mixing operation of the compound of formula II with the enantiomerically pure auxiliary is Usually carried out at temperatures from about 20° C. up to the boiling point of the employed solvent or solvent mixture, preferably at elevated temperatures up to the boiling point, for example at temperatures from about 20° C. to about 60° C., or at temperatures from about 40° C. to about 60° C., or at temperatures from about 40° C. up to the boiling point. The mixing Usually takes place over a certain time period, for example over a period of from about 1 hour to about 5 hours. In order to ensure a complete reaction of the compound of formula II with the auxiliary, the mixture is Usually held at temperature for some time.

The fractional crystallization can be initiated by cooling a heated mixture comprising the compound of formula II and the enantiomerically pure auxiliary, and/or partial evaporation of the solvent, and/or adding a further solvent, and/or adding seed crystals. The cooling is favorably performed slowly until crystals comprising the salt composed of the compound of formula I and the enantiomerically pure auxiliary precipitate. For completion of the crystallization, the mixture is Usually cooled to end temperatures of about 0° C. to about 30° C., in particular to temperatures of about 5° C. to about 20° C. The crystals comprising the salt composed of the compound of formula I and the enantiomerically pure auxiliary are separated and washed with a suitable solvent. The separation can take place by filtration or centrifugation, for example. Suitable solvents are, for example, esters such as n-butyl acetate, ethyl acetate or isopropyl acetate, or ethers such as diisopropyl ether or methyl tert-butyl ether. If desired, the resulting crystals can be dried, for example at elevated temperatures such as at about 60° C., under reduced pressure or at atmospheric pressure.

The remaining mother liquor, from which the crystals comprising the salt composed of the compound of formula I and the enantiomerically pure auxiliary have been separated, comprises the salt, remaining in solution, composed of the undesired opposite enantiomer of the compound of formula I and the enantiomerically pure auxiliary. After work-up and separation of the compound of formula I from the enantiomerically pure auxiliary, the undesired enantiomer can optionally be racemized, for example via base-induced racemization of an anhydride or active ester formed in situ, and subjected to a further racemate resolution in accordance with the aforementioned process, i.e., the undesired enantiomer can be recycled.

The isolation of the desired compound of formula I from the separated crystals, in which it is present in the form of the salt with the enantiomerically pure auxiliary, can be performed according to methods known to the person skilled in the art. For example, the crystals comprising the salt composed of the compound of formula I and the enantiomerically pure auxiliary can be suspended or dissolved in a suitable solvent, and the suspension or solution admixed with a suitable acid, for example sulfuric acid, for example at temperatures from about 10° C. to about 30° C. such as at room temperature. The auxiliary then dissolves, or remains in solution, and the compound of formula I generally precipitates and can be separated in the form of a solid, or otherwise can be obtained by standard procedures. Suitable solvents are, for example, alcohols such as methanol, ethanol and isopropanol, or esters such as ethyl acetate, isopropyl acetate and n-butyl acetate, or mixtures of solvents including mixtures of alcohols with water. The explanations given above with respect to the procedures for obtaining the salt composed of the compound of formula I and the enantiomerically pure auxiliary apply correspondingly to the procedures for obtaining the compound of formula I.

The invention also relates to a process for obtaining a compound of formula IV or a salt thereof,

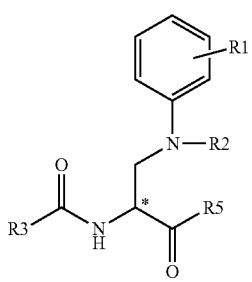

IV wherein
R1, R2 and R3 are defined as in the compound of formula I;
R5 is —NH$_2$, —N(H)—R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl;
which comprises
a) mixing a compound of formula II, wherein R1, R2 and R3 are defined as in the compound of formula I, in an organic solvent or a mixture of organic solvents with an enantiomerically pure auxiliary;
b) separating the salt composed of enantiomerically pure auxiliary and compound of formula I, by fractional crystallization;
c) isolating the compound of formula I from the salt composed of enantiomerically pure auxiliary and compound of formula I; and
d) converting the resulting compound of formula I with ammonia or an amine of the formula H$_2$N—R6 or HN(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, into the compound of formula IV or a salt thereof.

In one embodiment, the invention relates to a process for obtaining a compound of formula IV or a salt thereof, wherein
R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R3 is phenyl, methyl or —O—C(CH$_3$)$_3$;
R5 is —NH$_2$, —N(H)—R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl;
which comprises
a) mixing a compound of formula II, wherein R1, R2 and R3 are defined as in the compound of formula I, in an organic solvent or a mixture of organic solvents selected from the series consisting of n-butyl acetate, ethyl acetate, isopropyl acetate, diisopropyl ether, methyl tert-butyl ether and diethyl ether, with an enantiomerically pure auxiliary selected from the series consisting of (S)-1-phenylethylamine, (R)-1-phenylethylamine, (S)-1-naphthylethylamine, (R)-1-naphthylethylamine, (S)-1-cyclohexylethylamine, (R)-1-cyclohexylethylamine, (S)-1-cyclopropylethylamine and (R)-1-cyclopropylethylamine;
b) separating the salt composed of enantiomerically pure auxiliary and compound of formula I, by fractional crystallization;
c) isolating the compound of formula I from the salt composed of enantiomerically pure auxiliary and compound of formula I; and
d) converting the resulting compound of formula I with ammonia or an amine of the formula H$_2$N—R6 or HN(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, into the compound of formula IV or a salt thereof.

In one embodiment, the group R5 in the compounds and processes according to the invention outlined above and below, such as the compounds of formula IV, is —NH$_2$ or —N(H)—R6, in another embodiment it is —NH$_2$.

In one embodiment, the group R6 in the compounds and processes according to the invention outlined above and below, such as the compounds of formula IV, is (C$_1$-C$_4$)-alkyl, in another embodiment it is methyl.

The explanations given above, such as with respect to the groups R1, R2 and R3 or process steps a), b) and c), apply correspondingly to the compounds of formula IV and the process for their preparation defined afore. Process step d) can be carried out, for example, according to methods, and under reaction conditions, for the formation of carboxamides from carboxylic acids which are known to the person skilled in the art and are described, for example, in M. B. Smith and J. March, March's Advanced Organic Chemistry, 5th edition, Wiley-Interscience, New York, 2001. In general, for the formation of a carboxamide the carboxylic acid is activated with a suitable reagent, such as 1,1'-carbonyldiimidazole or a carbodiimide like N-(3-dimethylaminopropyl)-N'-ethylcarbodiimide hydrochloride, in an inert solvent such as an ether like tetrahydrofuran or acetonitrile at temperatures from about −20° C. up to boiling point of the solvent, and converted into the respective amide of formula IV by adding ammonia or the desired amine.

The invention also relates to a process for obtaining a compound of formula III or a salt thereof,

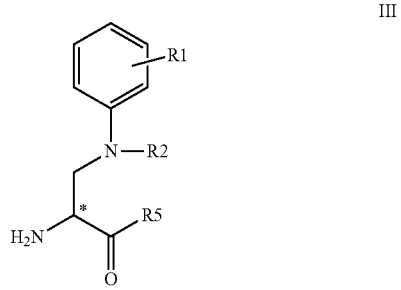

III wherein R1 and R2 are defined as in the compound of formula I;
R5 is —NH$_2$, —N(H)—R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl;
which comprises
a) mixing a compound of formula II, wherein R1, R2 and R3 are defined as in the compound of formula I, in an organic solvent or a mixture of organic solvents with an enantiomerically pure auxiliary;
b) separating the salt composed of enantiomerically pure auxiliary and compound of formula I, by fractional crystallization;
c) isolating the compound of formula I from the salt composed of enantiomerically pure auxiliary and compound of formula I;
d) converting the resulting compound of formula I with ammonia or an amine of the formula H$_2$N—R6 or HN(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, into a compound of formula IV or a salt thereof; and
e) converting the resulting compound of formula IV or salt thereof into the compound of formula III or a salt thereof.

In one embodiment, the invention relates to a process for obtaining a compound of formula III or a salt thereof, wherein R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R5 is —NH$_2$, —N(H)—R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl;
which comprises
a) mixing a compound of formula II, wherein R1, R2 and R3 are defined as in the compound of formula I, in an organic solvent or a mixture of organic solvents selected from the series consisting of n-butyl acetate, ethyl acetate, isopropyl acetate, diisopropyl ether, methyl tert-butyl ether and diethyl ether, with an enantiomerically pure auxiliary selected from the series consisting of (S)-1-phenylethylamine, (R)-1-phenylethylamine, (S)-1-naphthylethylamine, (R)-1-naphthylethylamine, (S)-1-cyclohexylethylamine, (R)-1-cyclohexylethylamine, (S)-1-cyclopropylethylamine and (R)-1-cyclopropylethylamine;
b) separating the salt composed of enantiomerically pure auxiliary and compound of formula I, by fractional crystallization;
c) isolating the compound of formula I from the salt composed of enantiomerically pure auxiliary and compound of formula I;
d) converting the resulting compound of formula I with ammonia or an amine of the formula H$_2$N—R6 or HN(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, into a compound of formula IV or a salt thereof; and
e) converting the resulting compound of formula IV or a salt thereof into the compound of formula III or a salt thereof.

The explanations given above, such as with respect to the groups R1, R2, R3 and R5 or process steps a), b), c) and d), apply correspondingly to the compounds of formula III and the process for their preparation defined afore. Process step e) can be carried out, for example, according to methods, and under reaction conditions, for the cleavage of carboxamides and carbamates to give the amines which are known to the person skilled in the art and are described, for example, in M. B. Smith and J. March, March's Advanced Organic Chemistry, 5th edition, Wiley-Interscience, New York, 2001; or in D. L. Flynn et al., J. Org. Chem. 1983, 48, 2424; or in M. J. Burk et al., J. Org. Chem. 1997, 62, 7054. For example, the cleavage of a tert-butoxycarbonyl group representing the group R3-C(O)— in the compounds of formula IV to give compounds of formula III can be performed under standard conditions such as treatment with trifluoroacetic acid (TFA), hydrochloric acid or p-toluenesulfonic acid in a suitable solvent, such as a chlorinated hydrocarbon like dichloromethane or water, at temperatures from about 0° C. to about 50° C.

The preparation of salts of compounds of formulae III and IV capable of salt formation, including their stereoisomeric forms, in process step d) and e), respectively, can be performed according to standard procedures known per se. If the compounds of formulae III and IV contain acid groups, stable alkali metal salts, alkaline earth metal salts and optionally substituted ammonium salts and amidinium salts can be prepared Using basic reagents such as hydroxides, carbonates, hydrogencarbonates, alcoholates, ammonia or organic bases, for example amines like trimethylamine, triethylamine, ethanolamine, diethanolamine, triethanolamine, trometamol, amidines like 1,8-diazabicyclo[5.4.0]undec-7-ene, or basic amino acids like lysine, ornithine or arginine. If the compounds of formulae III and IV contain basic groups, stable acid addition salts can be prepared Using acidic reagents including inorganic acids and organic acids like hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethanesulfonic acid, 2-hydroxyethanesulfonic acid, acetic acid, oxalic acid, tartaric acid, succinic acid, glycerolphosphoric acid, lactic acid, malic acid, adipic acid, citric acid, fumaric acid, maleic acid, gluconic acid, glucuronic acid, palmitic acid or trifluoroacetic acid. These explanations apply likewise to salts of other compounds according to the invention, such as compounds of formulae I, II or IIb, which are capable of salt formation, and which can be employed in the processes of the invention, or obtained by them, or are a subject of the invention, just so in the form of their salts.

Under these conditions, enantiomeric purities of >99% ee are achieved in the preparation of compounds of formulae I, III and IV according to the processes of the invention without the need for repeated additional enrichment steps such as recrystallizations.

The starting compounds of formula II are known or can be prepared according to, or analogously to, procedures described in the literature. For example, compounds of formula VI, which can be synthesized analogously as described in K. El Abdioui et al., Bull. Soc. Chim. Belg. 1997, 106, 425 or P. M. T. Ferreira et al., J. Chem. Soc., Perkin Trans. 1, 1999, 3697, can be reacted with amines of formula V in a suitable solvent, such as an ether like tetrahydrofuran or diisopropyl ether, favorably in the presence of a base such as an alkali metal alkoxide like lithium tert-butoxide or an alkali metal carbonate like cesium carbonate at temperatures from about −10° C. to about 30° C., to give compounds of formula IIa.

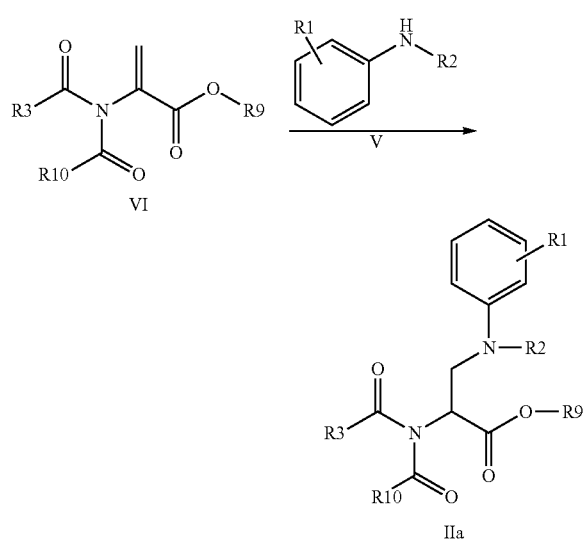

The resulting compound of formula IIa can be converted into a compound of formula IIb, in which R4 is a hydrogen atom or an alkali metal ion such as lithium, sodium, potassium, rubidium or cesium, i.e. the group R4-O—C(O)— is a carboxylic acid group or an alkali metal salt thereof, by treatment with an alkali metal hydroxide such as lithium hydroxide (LiOH), sodium hydroxide (NaOH), potassium hydroxide (KOH), rubidium hydroxide (RbOH) or cesium hydroxide (CsOH), for example sodium hydroxide, in a suitable solvent or a mixture of solvents, such as water or an ether like tetrahydrofuran or dioxane or a mixture of water and an ether, at temperatures from about 0° C. to about 120° C., for example temperatures from about 20° C. to about 80° C., or temperatures from about 20° C. to about 60° C. The reaction time generally is from about 0.5 hours to about 8 hours, depending on the composition of the reaction mixture and the selected temperature range. The resulting compound of formula IIb is then isolated from the reaction mixture by standard procedures, as applies to the isolation of all compounds prepared according to the present invention, for example by aqueous work-up, optionally with addition of an acid such as sulfuric acid, and extraction with a suitable solvent, for example ethyl acetate or dichloromethane, or crystallization.

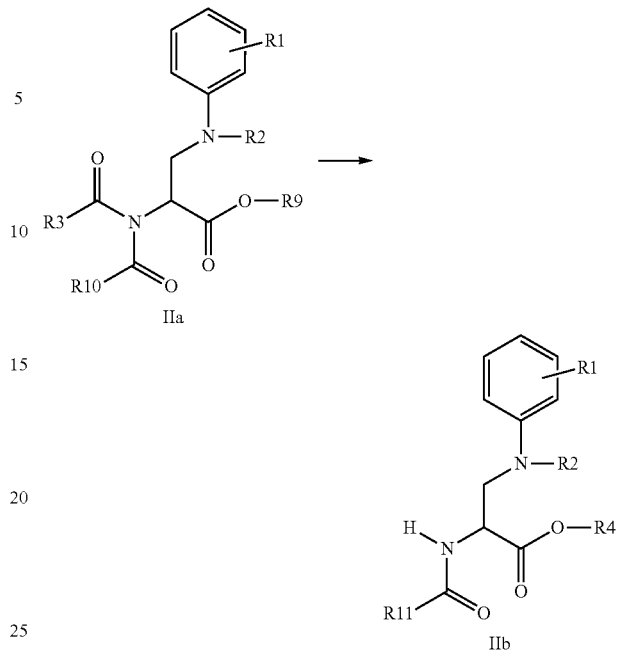

In the compounds of formulae VI, V, IIa and IIb,

R1, R2 and R3 are defined as in the compounds of formula I;

R4 is a hydrogen atom or an alkali metal ion;

R9 is $(C_1-C_4)$-alkyl or —CH(R8)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, and wherein R8 is a hydrogen atom or $(C_1-C_4)$-alkyl;

R10 and R11 are, independently of one another, a hydrogen atom, or $(C_1-C_4)$-alkyl, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —$NO_2$, —O—$(C_1-C_4)$-alkyl, F, Cl and Br, or —O—$C(CH_3)_3$, or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —$NO_2$, —O—$CH_3$, F, Cl and Br, and wherein R7 is a hydrogen atom or $(C_1-C_4)$-alkyl.

The simultaneous cleavage of two different protective groups, i.e. one of the acyl groups R3-C(O)— and R10-C(O)— at the nitrogen atom and the ester function R9-O—C(O)— protecting the carboxylic acid group, in the conversion of the compounds of formula IIa into the compounds of formula IIb surprisingly proceeds in a selective manner and without by-product formation, and thus produces compounds of formula IIb in high yields. This novel, highly selective one-pot reaction is thus optimally suited for industrial production.

The invention thus also relates to a process for obtaining a compound of formula IIb,

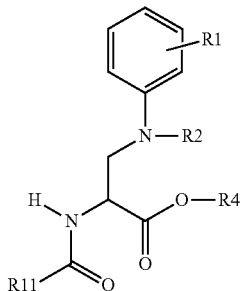

IIb wherein
R1 and R2 are defined as in the compound of formula I;
R4 is a hydrogen atom or an alkali metal ion;
R11 is a hydrogen atom,
or $(C_1\text{-}C_4)$-alkyl,
or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —$NO_2$, —O—$(C_1\text{-}C_4)$-alkyl, F, Cl and Br,
or —O—$C(CH_3)_3$,
or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —$NO_2$, —O—$CH_3$, F, Cl and Br, and wherein R7 is a hydrogen atom or $(C_1\text{-}C_4)$-alkyl;
which comprises reacting a compound of formula IIa,

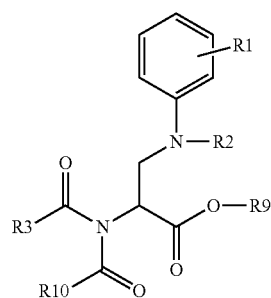

IIa wherein
R1, R2 and R3 are defined as in the compound of formula I;
R9 is $(C_1\text{-}C_4)$-alkyl or —CH(R8)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, and wherein R8 is a hydrogen atom or $(C_1\text{-}C_4)$-alkyl;
R10 is a hydrogen atom,
or $(C_1\text{-}C_4)$-alkyl,
or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —$NO_2$, —O—$(C_1\text{-}C_4)$-alkyl, F, Cl and Br,
or —O—$C(CH_3)_3$,
or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —$NO_2$, —O—$CH_3$, F, Cl and Br, and wherein R7 is a hydrogen atom or $(C_1\text{-}C_4)$-alkyl;
with an alkali metal hydroxide to give a compound of formula IIb.

The explanations given above, such as with respect to the groups R1, R2 and R3, apply correspondingly to the compounds of formulae IIb and IIa and the process for their conversion. Explanations relating specifically to the conversion of the compounds of formula IIa into compounds of formula IIb are already given afore.

In one embodiment, the invention relates to a process for obtaining a compound of formula IIb, wherein
R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R4 is a hydrogen atom;
R11 is phenyl, methyl or —O—$C(CH_3)_3$;
which comprises reacting a compound of formula IIa, wherein
R1 and R2 are defined as in the compound of formula IIb;
R3 and R10 are, independently of one another, phenyl, methyl or —O—$C(CH_3)_3$;
R9 is methyl or ethyl;
with an alkali metal hydroxide to give a compound of formula IIb.

In one embodiment, the group R4 in the compounds and processes according to the invention outlined above and below, such as the compounds of formula IIb, is a hydrogen atom or a sodium ion, in another embodiment it is a hydrogen atom.

In one embodiment, the group R9 in the compounds and processes according to the invention outlined above and below, such as the compounds of formula IIa, is $(C_1\text{-}C_4)$-alkyl, in another embodiment it is $(C_1\text{-}C_3)$-alkyl, in another embodiment it is methyl or ethyl, in another embodiment it is methyl.

In one embodiment, the group R10 in the compounds and processes according to the invention outlined above and below, such as the compounds of formula IIa, is methyl, —O—$C(CH_3)_3$ or —O—CH(R7)-aryl, wherein R7 is a hydrogen atom and aryl is unsubstituted phenyl, in another embodiment it is —O—$C(CH_3)_3$ or —O—CH(R7)-aryl, wherein R7 is a hydrogen atom and aryl is unsubstituted phenyl, in another embodiment it is methyl, in another embodiment it is —O—$C(CH_3)_3$, in another embodiment it is —O—CH(R7)-aryl, wherein R7 is a hydrogen atom and aryl is unsubstituted phenyl.

In one embodiment, the group R11 in the compounds and processes according to the invention outlined above and below, such as the compounds of formula IIb, is methyl, —O—$C(CH_3)_3$ or —O—CH(R7)-aryl, wherein R7 is a hydrogen atom and aryl is unsubstituted phenyl, in another embodiment it is —O—$C(CH_3)_3$ or —O—CH(R7)-aryl, wherein R7 is a hydrogen atom and aryl is unsubstituted phenyl, in another embodiment it is methyl, in another embodiment it is —O—C(CH$_3$)$_3$, in another embodiment it is —O—CH(R7)-aryl, wherein R7 is a hydrogen atom and aryl is unsubstituted phenyl.

A further aspect of the present invention are the 2,3-diaminopropionic acid derivatives, or 2,3-diaminopropanoic acid derivatives, of formulae I, III and IV per se, also in the form of a mixture of the enantiomers, and in the form of their salts, which are likewise provided by the invention. The term "mixture of enantiomers" is to be understood here in particular as meaning a mixture of enantiomers in which one enantiomer is enriched compared to its opposite enantiomer, or is present in substantially pure form and, for example, the enantiomeric excess ee is >90% in one embodiment, or >95% in another embodiment, or >98% in another embodiment, or >99% in another embodiment.

Thus, the invention also relates to novel compounds of formula I,

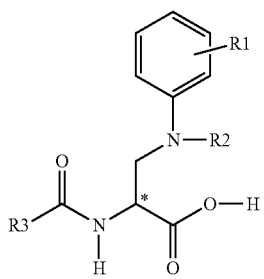

I wherein
R1 is a hydrogen atom, F, Cl, I, Br, (C$_1$-C$_4$)-alkyl or —CN;
R2 is a heteroaryl residue selected from the series consisting of pyrrole, furan, thiophene, imidazole, pyrazole, oxazole, isoxazole, thiazole, isothiazole, tetrazole, 1,2,3,5-oxathiadiazole 2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-,
or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-;
R3 is a hydrogen atom,
or (C$_1$-C$_4$)-alkyl,
or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —NO$_2$, —O—(C$_1$-C$_4$)-alkyl, F, Cl and Br,
or —O—C(CH$_3$)$_3$,
or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —NO$_2$, —O—CH$_3$, F, Cl and Br, and wherein R7 is a hydrogen atom or (C$_1$-C$_4$)-alkyl;
provided that the compound of formula I is not (S)-2-benzyloxycarbonylamino-3-diphenylamino-propionic acid, i.e. the compound of formula I wherein R1 is a hydrogen atom, R2 is unsubstituted phenyl, R3 is —CH(R7)-aryl wherein aryl is unsubstituted phenyl and R7 is a hydrogen atom, and the chiral carbon atom has S configuration.

In one embodiment, the invention relates to novel compounds of formula I, wherein
R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R3 is phenyl, methyl or —O—C(CH$_3$)$_3$.

Another aspect of the invention relates to novel compounds of formula II, which are the starting compounds for the preparation of the compounds of formula I according to the invention,

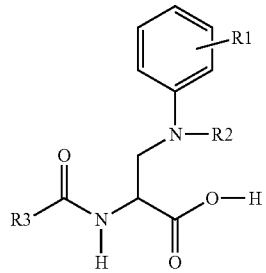

II wherein
R1 is a hydrogen atom, F, Cl, I, Br, (C$_1$-C$_4$)-alkyl or —CN;
R2 is a heteroaryl residue selected from the series consisting of pyrrole, furan, thiophene, imidazole, pyrazole, oxazole, isoxazole, thiazole, isothiazole, tetrazole, 1,2,3,5-oxathiadiazole 2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-,
or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-;

R3 is a hydrogen atom, or (C$_1$-C$_4$)-alkyl, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —NO$_2$, —O—(C$_1$-C$_4$)-alkyl, F, Cl and Br, or —O—C(CH$_3$)$_3$, or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —NO$_2$, —O—CH$_3$, F, Cl and Br, and wherein R7 is a hydrogen atom or (C$_1$-C$_4$)-alkyl.

In one embodiment, the invention relates to novel compounds of formula II, wherein R1 is a hydrogen atom, F, Cl, I or Br;

R2 is phenyl, pyridinyl, pyrimidinyl or thiazolyl, wherein phenyl, pyridinyl, pyrimidinyl and thiazolyl are unsubstituted or substituted by fluorine or chlorine;

R3 is phenyl, methyl or —O—C(CH$_3$)$_3$.

The invention further relates to compounds of formula III selected from the series consisting of (S)-2-amino-3-(phenyl-pyrimidin-2-ylamino)-propanoic acid amide (formula IIIa), or a salt thereof, and (R)-2-amino-3-(phenyl-pyrimidin-2-ylamino)-propanoic acid amide (formula IIb), or a salt thereof. In one embodiment, the compound of formula III is the compound of formula IIIa, or a salt thereof, and in another embodiment it is the compound of formula IIIb, or a salt thereof.

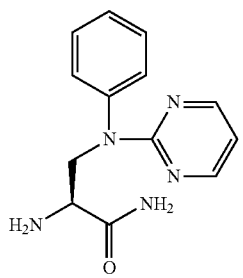

IIIa

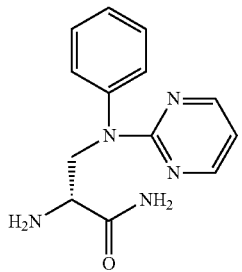

IIIb

The invention further relates to novel compounds of formula IV,

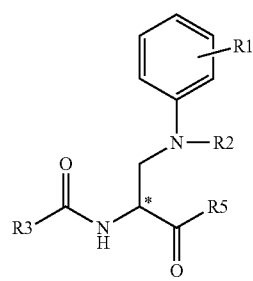

IV wherein

R1 is a hydrogen atom, F, Cl, I, Br, (C$_1$-C$_4$)-alkyl or —CN,

R2 is a heteroaryl residue selected from the series consisting of pyrrole, furan, thiophene, imidazole, pyrazole, oxazole, isoxazole, thiazole, isothiazole, tetrazole, 1,2,3,5-oxathiadiazole 2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-;

R3 is a hydrogen atom, or (C$_1$-C$_4$)-alkyl, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —NO$_2$, —O—(C$_1$-C$_4$)-alkyl, F, Cl and Br, or —O—C(CH$_3$)$_3$, or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —NO$_2$, —O—CH$_3$, F, Cl and Br, and wherein R7 is a hydrogen atom or (C$_1$-C$_4$)-alkyl;

R5 is —NH$_2$, —N(H)—R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl.

In one embodiment, the invention relates to novel compounds of formula IV, wherein
R1 is a hydrogen atom, F, Cl, I or Br;
R2 is phenyl, pyridinyl, pyrimidinyl or thiazolyl, wherein phenyl, pyridinyl, pyrimidinyl and thiazolyl are unsubstituted or substituted by fluorine or chlorine;
R3 is phenyl, methyl or —O—C(CH$_3$)$_3$;
R5 is —NH$_2$.

As already indicated, the explanations given above and the embodiments defined above, such as with respect to the groups R1, R2, R3 and R5 apply correspondingly to the compounds of formulae I, II, III and IV which are a subject of the invention as compounds per se. The compounds of formulae I, II, III and IV are suitable as intermediate compounds for the preparation of IkB kinase inhibitors as described in WO 01/30774 A1, WO 2004/022553 A1 and US 2007/0142417 A1, for example.

The invention is illustrated below in more detail by reference to examples. End products are generally characterized by $^1$H-NMR (400 MHz, in DMSO-d$_6$, unless indicated otherwise), mass spectrometry and optionally chiral HPLC analysis. Temperature data are given in degree Celsius. RT means room temperature (about 22° C. to 26° C.). Any abbreviations Used are either explained or correspond to standard conventions.

EXAMPLE 1

Preparation of 2-tert-butoxycarbonylamino-3-(phenyl-pyrimidin-2-ylamino)-propanoic acid Step 1
A solution of 2-anilino-pyrimidine (71 g, 415 mmol; prepared in accordance with T. Matsukawa et al., Yakugaku Zasshi 1951, 71, 933) and lithium tert-butoxide (14 g, 175 mmol) in tetrahydrofuran (170 ml) is cooled to −5° C. At this temperature, a solution of methyl 2-[bis(tert-butoxycarbonyl)]amino-prop-2-enoate (100 g, 332 mmol; prepared in accordance with K. El Abdioui et al., Bull. Soc. Chim. Belg. 1997, 106, 425) in tetrahydrofuran (70 ml) is added, the mixture is stirred for further 4 h at −5° C. and then warmed to RT.
Step 2
The reaction mixture obtained in step 1 is admixed with 23% sodium hydroxide solution (290 g, 1.6 mol) and heated under reflux for 7 h. Tetrahydrofuran is distilled off, the reaction solution is cooled to RT and extracted with methyl tert-butyl ether (400 ml). The aqueoUs phase is diluted with isopropanol (260 ml) and admixed with 2N sulfuric acid until pH 4 is reached. The precipitated solid is filtered off with suction and dried to give 2-tert-butoxycarbonylamino-3-(phenyl-pyrimidin-2-ylamino)-propanoic acid (82 g, 69%) as a cream-colored solid.
C$_{18}$H$_{22}$N$_4$O$_4$, M=358.40 g/mol; MS (ESI): m/z=359 ((M+1)$^+$, 100%); $^1$H-NMR (400 MHz, DMSO-d$_6$): δ=12.60 (bs, 1 H), 8.36 (d, J=4.8 Hz, 2 H), 7.42-7.36 (m, 2 H), 7.30-7.21 (m, 3 H), 7.05 (t, J=8.3 Hz, 1 H), 6.76 (t, J=4.8 Hz, 1 H), 4.48-4.30 (m, 2 H), 4.12-4.01 (m, 1 H), 1.31 (s, 9 H) ppm; melting point: 165° C. (decomposition).

EXAMPLE 2

Preparation of (S)-1-phenylethyl-ammonium (S)-2-tert-butoxycarbonylamino-3-(phenyl-pyrimidin-2-ylamino)-propanoate Step 1
A suspension of 2-tert-butoxycarbonylamino-3-(phenyl-pyrimidin-2-ylamino)-propanoic acid prepared as in Example 1 (120 g, 335 mmol) in n-butyl acetate (1000 ml) is admixed at 50° C. with (S)-1-phenylethyl-amine (38.5 g, 318 mmol; 99.7% chemical purity, 99.3% ee (enantiomeric excess); BASF), the mixture stirred for further 2 h at this temperature and then cooled to RT. The precipitated solid is filtered off with suction and dried to give a cream-colored crystalline crude product (83.9 g) which is Used directly in step 2.
Step 2
The crude product (83.9 g) obtained in step 1 is heated under reflux for 2 h in ethyl acetate (590 ml) and then cooled to 5° C. The solid is filtered off with suction and dried to give (S)-1-phenylethyl-ammonium (S)-2-tert-butoxycarbonylamino-3-(phenyl-pyrimidin-2-ylamino)-propanoate (72.1 g, 45%, 99.5% de (diastereomeric excess)) as a colorless solid.
C$_{26}$H$_{33}$N$_5$O$_4$, M=479.58 g/mol; $^1$H-NMR (400 MHz, methanol-d$_4$): δ=8.31 (d, J=5.0 Hz, 2 H), 7.51-7.41 (m, 7 H), 7.39-7.30 (m, 3 H), 6.69 (m, 1 H), 4.55 (m, 1 H), 4.43 (m, 1 H), 4.40 (q, J=7.0 Hz, 1 H), 4.18 (m, 1 H), 1.60 (d, J=7.0 Hz, 3 H), 1.31 (s, 9 H) ppm; melting point: 174° C.

EXAMPLE 3

Preparation of (S)-2-tert-butoxycarbonylamino-3-(phenyl-pyrimidin-2-ylamino)-propanoic acid A sUspension of (S)-1-phenylethyl-ammonium (S)-2-tert-butoxycarbonylamino-3-(phenyl-pyrimidin-2-ylamino)-propanoate (37.2 g, 77.5 mmol, 99.5% de) in aqueoUs isopropanol (50% strength, 90 ml) is admixed with 1N sulfuric acid (97 ml, 48.5 mmol) and stirred for 1 h at RT. The solid is filtered off with suction and dried to give (S)-2-tert-butoxycarbonylamino-3-(phenyl-pyrimidin-2-ylamino)-propanoic acid (26.5 g, 95%, >99.9% ee) as a colorless solid.
C$_{18}$H$_{22}$N$_4$O$_4$, M=358.40 g/mol; MS (ESI): m/z=359 ((M+1)$^+$, 100%); $^1$H-NMR (400 MHz, DMSO-d$_6$): δ=12.60 (bs, 1 H), 8.36 (d, J=4.8 Hz, 2 H), 7.42-7.36 (m, 2H), 7.30-7.21 (m, 3 H), 7.05 (t, J=8.3 Hz, 1 H), 6.76 (t, J=4.8 Hz, 1 H), 4.48-4.30 (m, 2 H), 4.12-4.01 (m, 1 H), 1.31 (s, 9 H) ppm; HPLC (column: Chiralpak AD-H, 250×4.6 mm, n-heptane+0.1% TFA:ethanol+0.1% TFA 95:5, 1 ml/min, 254 nm): retention time [min]=19.1 (S), 21.4 (R).

EXAMPLE 4

Preparation of (S)-2-tert-butoxycarbonylamino-3-(phenyl-pyrimidin-2-ylamino)-propanoic acid amide A suspension of (S)-2-tert-butoxycarbonylamino-3-(phenyl-pyrimidin-2-ylamino)-propanoic acid (11.9 g, 33.2 mmol, >99.9% ee) in acetonitrile (36 ml) is admixed at −15° C. with a solution of 1,1'-carbonyldiimidazole (8.36 g, 51.6 mmol) in acetonitrile (125 ml), and the reaction mixture is stirred for 2 h at this temperature. Ammonia (4.0 g, 222 mmol) is then introduced, and the mixture is stirred for further 1 h and then adjUsted to pH 4.5 Using 2N sulfuric acid. Acetonitrile is distilled off, and the precipitated solid is filtered off with suction and dried to give (S)-2-tert-butoxycarbonylamino-3-(phenyl-pyrimidin-2-ylamino)-propanoic acid amide (11.3 g, 95%, >99.9% ee) as a colorless solid.
C$_{18}$H$_{23}$N$_6$O$_3$, M=357.42 g/mol; MS (ESI): m/z=358 ((M+1)$^+$, 100%); $^1$H-NMR (400 MHz, DMSO-d$_6$): δ=8.41 (d, J=5.0 Hz, 2 H), 7.50-7.43 (m, 2 H), 7.35-7.28 (m, 4 H), 7.17 (s, 1 H), 6.79 (t, J=5.0 Hz, 1 H), 6.68 (d, J=9.0 Hz, 1H), 4.36 (m, 1 H), 4.23 (m, 1 H), 4.08 (m, 1 H), 1.31 (s, 9 H) ppm;

EXAMPLE 5

Preparation of (S)-2-amino-3-(phenyl-pyrimidin-2-ylamino)-propanoic acid amide (S)-2-tert-Butoxycarbonylamino-3-(phenyl-pyrimidin-2-ylamino)-propanoic acid amide (48.5 g, 136 mmol, >99.9% ee) is introduced at 40° C. in portions into hydrochloric acid (16% strength, 80 ml), and the resulting solution is stirred for 1 h at this temperature. After cooling to 5° C., the pH is adjUsted to 10 by adding concentrated potassium hydroxide solution. The precipitated solid is filtered off with suction and dried to give (S)-2-amino-3-(phenyl-pyrimidin-2-ylamino)-propanoic acid amide (35.3 g, 80% yield, 79% content, 99.8% ee) as a colorless solid, which can be further reacted or else crystallized again from aqueoUs solution, as desired.

$C_{13}H_{16}N_6O$, M=257.29 g/mol; MS (ESI): m/z=258 ((M+1)$^+$, 100%); $^1$H-NMR (400 MHz, DMSO-d$_6$): δ=8.37 (d, J=4.8 Hz, 2 H), 7.50-7.39 (m, 5 H), 7.28 (t, J=7.3 Hz, 1 H), 7.06 (bs, 1 H), 6.73 (t, J=4.8 Hz, 1 H), 4.30 (dd, J=9.6 and 14.4 Hz, 1 H), 3.92 (dd, J=5.3 and 14.3 Hz, 1 H), 3.43 (dd, J=5.2 and 9.5 Hz, 1 H), 1.83 (bs, 2 H) ppm; HPLC (column: Chiralpak AS, 250×4.6 mm, ethanol+0.1% diethylamine:methanol+0.1% diethylamine 50:50, 1 ml/min, 231 nm): retention time [min]=4.5 (S), 6.8 (R); melting point: 139° C.

EXAMPLE 6

2-tert-Butoxycarbonylamino-3-(phenyl-pyridin-2-ylamino)-propanoic acid

Step 1

A suspension of 2-anilino-pyridine (3.40 g, 20.0 mmol) and cesium carbonate (3.26 g, 10.0 mmol) in diisopropyl ether (12 ml) is admixed with methyl 2-[bis(tert-butoxycarbonyl)]amino-prop-2-enoate (6.03 g, 20.0 mmol) and heated under reflux for 23 h. The sUspension is filtered hot, and the solution obtained is evaporated under reduced pressure.

Step 2

The crude product obtained in step 1 is dissolved in tetrahydrofuran (30 ml), admixed with 32% strength sodium hydroxide solution (10 ml) and heated under reflux for 4 h. The resulting suspension is filtered, and the solution obtained is admixed with water. Tetrahydrofuran is distilled off and the aqueous solution is extracted with methyl tert-butyl ether. The aqueoUs phase is diluted with isopropanol (30 ml) and admixed with 2N sulfuric acid until pH 4 is reached. The precipitated solid is filtered off with suction and dried to give 2-tert-butoxycarbonylamino-3-(phenyl-pyridin-2-ylamino)-propanoic acid (2.25 g, 32%) as a cream-colored solid.

$C_{19}H_{23}N_3O_4$, M=357.41 g/mol; MS (ESI): m/z=358 ((M+1)$^+$, 100%); $^1$H-NMR (400 MHz, methanol-d$_4$): δ=8.17 (m, 1H), 7.51-7.32 (m, 6 H), 6.73 (t, J=6.1 Hz, 1 H), 6.39 (m, 1 H), 4.41 (m, 2 H), 4.28 (m, 1 H), 1.39 (s, 9H) ppm; melting point 140° C. (decomposition).

EXAMPLE 7

Methyl 2-[bis(tert-butoxycarbonyl)]amino-3-(phenyl-pyridin-2-ylamino)-propanoate An aliquot of the reaction mixture obtained in step 1 of example 6 is diluted with diisopropyl ether and admixed with 2N sulfuric acid until pH 5 is reached. The precipitated solid is filtered off with suction and dried to give methyl 2-[bis(tert-butoxycarbonyl)]amino-3-(phenyl-pyridin-2-ylamino)-propanoate as a yellow solid.

$C_{25}H_{33}N_3O_6$, M=471.56 g/mol; MS (ESI): m/z=472 ((M+1)$^+$, 100%); $^1$H-NMR (400 MHz, DMSO-d$_6$): δ=8.17 (d, J=3.9 Hz, 1 H), 7.45 (m, 2 H), 7.38 (m, 1 H), 7.30-7.20 (m, 3 H), 6.67 (t, J=6.2 Hz, 1 H), 6.26 (d, J=8.6 Hz, 1 H), 5.71 (dd, J=4.3 and 10.1 Hz, 1 H), 4.67 (dd, J=4.3 and 14.1 Hz, 1 H), 4.17 (dd, J=10.3 and 14.1 Hz, 1 H), 3.67 (s, 3 H), 1.20 (s, 18 H) ppm; melting point 103° C.

EXAMPLE 8

(S)-1-Phenylethyl-ammonium (S)-2-tert-butoxycarbonylamino-3-(phenyl-pyridin-2-ylamino)-propanoate Step 1

A suspension of 2-tert-butoxycarbonylamino-3-(phenyl-pyridin-2-ylamino)-propanoic acid (6.80 g, 19.0 mmol) in diisopropyl ether (50 ml) is admixed at 60° C. with a solution of (S)-1-phenylethyl-amine (2.20 g, 18.2 mmol) in diisopropyl ether (10 ml). The mixture is stirred at this temperature for a further hour and then cooled to RT. The precipitated solid is filtered off with suction and dried to give a cream-colored crystalline crude product (3.50 g), which is directly used in step 2.

Step 2

The crude product (3.50 g) obtained in step 1 is heated under reflux for 1 h in diisopropyl ether (70 ml) and then cooled to RT. The solid is filtered off with suction and dried to give (S)-1-phenylethyl-ammonium (S)-2-tert-butoxycarbonylamino-3-(phenyl-pyridin-2-ylamino)-propanoate (2.40 g, 28%, 99.5% de) as a colorless solid.

$C_{27}H_{34}N_4O_4$, M=478.6 g/mol; $^1$H-NMR (400 MHz, methanol-d$_4$): δ=8.10 (m, 1 H), 7.50-7.25 (m, 11 H), 6.65 (m, 1 H), 6.38 (m, 1 H), 4.61 (m, 1 H), 4.40 (q, J=7.1 Hz, 1 H), 4.30 (m, 1 H), 4.05 (m, 1 H), 1.61 (d, J=7.1 Hz, 3 H), 1.30 (s, 9 H) ppm; melting point 131° C. to 136° C.

EXAMPLE 9

(S)-2-tert-Butoxycarbonylamino-3-(phenyl-pyridin-2-ylamino)-propanoic acid

A suspension of (S)-1-phenylethyl-ammonium (S)-2-tert-butoxycarbonylamino-3-(phenyl-pyridin-2-ylamino)-propanoate (2.25 g, 4.69 mmol, 99.5% de) in aqueous isopropanol (50% strength, 6 ml) is admixed with 1N sulfuric acid (6 ml, 5.85 mmol) and stirred for 2 h at RT. The solid is filtered off with suction and dried to give (S)-2-tert-butoxycarbonylamino-3-(phenyl-pyridin-2-ylamino)-propanoic acid (1.35 g, 81%, >99.9% ee) as a colorless solid.

$C_{19}H_{23}N_3O_4$, M=357.41 g/mol; MS (ESI): m/z=358 ((M+1)$^+$, 100%); $^1$H-NMR (400 MHz, methanol-d$_4$): δ=8.17 (m, 1H), 7.51-7.32 (m, 6 H), 6.73 (t, J=6.1 Hz, 1 H), 6.39 (m, 1 H), 4.41 (m, 2 H), 4.28 (m, 1 H), 1.39 (s, 9 H) ppm; HPLC (column: Chiralcel OD-H, 250×4.6 mm, n-heptane+0.1% TFA:ethanol+0.1% TFA 97:3, 1.2 ml/min, 240 nm): retention time [min]=9.7 (S), 11.5 (R); melting point 144° C. (decomposition).

What is claimed is:

1. A process for obtaining a compound of formula III or a salt thereof:

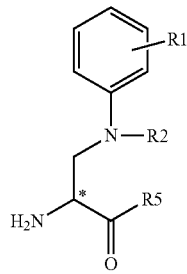

III wherein R1 is a hydrogen atom, F, Cl, I, Br, (C$_1$-C$_4$)-alkyl or —CN;

and R2 is a heteroaryl residue selected from the series consisting of pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline and β-carboline, wherein the heteroaryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted once, twice or three times, independently of each other, by substituents selected from the series consisting of (C$_1$-C$_5$)-alkyl, (C$_1$-C$_5$)-alkoxy, halogen, nitro, amino, trifluoromethyl, hydroxy, hydroxy-(C$_1$-C$_4$)-alkyl-, methylenedioxy, ethylenedioxy, formyl, acetyl, cyano, hydroxycarbonyl-, aminocarbonyl- and (C$_1$-C$_4$)-alkoxycarbonyl-;

R5 is —NH$_2$, —N(H)-R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl;

said process comprising a) mixing a compound of formula II:

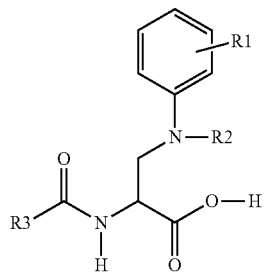

II wherein R1 and R2 are as defined above, and R3 is a hydrogen atom, or (C$_1$-C$_4$)-alkyl, or an aryl residue selected from the series consisting of phenyl, naphthyl, 1-naphthyl, 2-naphthyl, biphenylyl, 2-biphenylyl, 3-biphenylyl, 4-biphenylyl, anthryl and fluorenyl, wherein the aryl residue is unsubstituted or is substituted, independently of each other, once, twice or three times by substituents selected from the series consisting of —NO$_2$, —O—(C$_1$-C$_4$)-alkyl, F, Cl and Br, or —O—C(CH$_3$)$_3$, or —O—CH(R7)-aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl and is unsubstituted or is substituted, independently of each other, once, twice or three times by substituents selected from the series consisting of —NO$_2$, —O—CH$_3$, F, Cl and Br, and wherein R7 is a hydrogen atom or (C$_1$-C$_4$)-alkyl;

in an organic solvent or a mixture of organic solvents with an enantiomerically pure auxiliary;

b) separating the salt composed of enantiomerically pure auxiliary and compound of formula I:

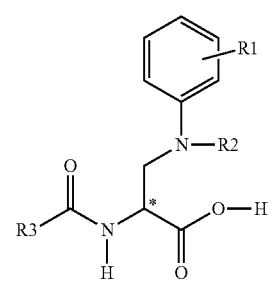

I by fractional crystallization;

c) isolating the compound of formula I from the salt composed of enantiomerically pure auxiliary and compound of formula I;

d) converting the resulting compound of formula I with ammonia or an amine of the formula H$_2$N-R6 or HN(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl, into a compound of formula IV:

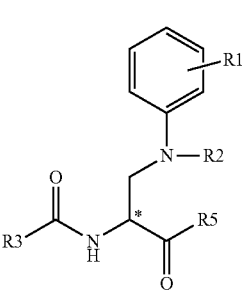

IV or a salt thereof; and e) converting the resulting compound of formula IV or salt thereof into the compound of formula III or a salt thereof.

2. The process as claimed in claim 1, wherein a compound of formula III or a salt thereof is obtained, wherein R1 is a hydrogen atom, F, CI, I or Br;

R2 is phenyl, pyridinyl, pyrimidinyl or thiazolyl, wherein phenyl, pyridinyl, pyrimidinyl and thiazolyl are unsubstituted or substituted by fluorine or chlorine;

R5 is —NH$_2$, —N(H)-R6 or —N(R6)$_2$, wherein R6 is (C$_1$-C$_4$)-alkyl or aryl, wherein the aryl residue is selected from the series consisting of phenyl, naphthyl, 1-naphthyl, 2-naphthyl, biphenylyl, 2-biphenylyl, 3-biphenylyl, 4-biphenylyl, anthryl and fluorenyl.

3. A compound of formula III, selected from the series consisting of (S)-2-amino-3-(phenyl-pyrimidin-2-ylamino)-propanoic acid amide (formula IIIa), or a salt thereof, and (R)-2-amino-3-(phenyl-pyrimidin-2-ylamino)-propanoic acid amide (formula IIIb), or a salt thereof:

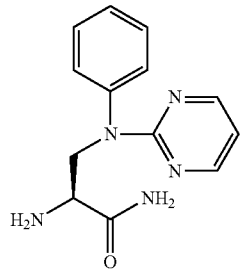

IIIa

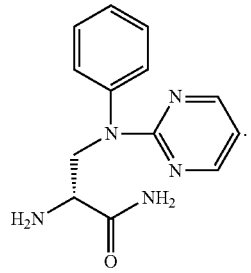

IIIb

* * * * *